United States Patent
Khan et al.

(10) Patent No.: US 12,408,959 B2
(45) Date of Patent: Sep. 9, 2025

(54) PLATE INSERTER SYSTEM AND METHOD

(71) Applicant: GLOBUS MEDICAL, INC., Audubon, PA (US)

(72) Inventors: Mohammed Khan, Saddle River, NJ (US); Colm McLaughlin, Glenside, PA (US); Julia Gambogi, Eagleville, NJ (US)

(73) Assignee: Globus Medical, Inc., Audubon, PA (US)

( * ) Notice: Subject to any disclaimer, the term of this patent is extended or adjusted under 35 U.S.C. 154(b) by 402 days.

(21) Appl. No.: 17/812,294

(22) Filed: Jul. 13, 2022

(65) Prior Publication Data

US 2024/0016528 A1 Jan. 18, 2024

(51) Int. Cl.
*A61B 17/80* (2006.01)
*A61B 17/16* (2006.01)
*A61B 17/70* (2006.01)

(52) U.S. Cl.
CPC ........ *A61B 17/808* (2013.01); *A61B 17/1604* (2013.01); *A61B 17/7059* (2013.01)

(58) Field of Classification Search
CPC ............. A61B 17/808; A61B 17/1604
See application file for complete search history.

(56) References Cited

U.S. PATENT DOCUMENTS

| | | | | |
|---|---|---|---|---|
| 5,279,575 A * | 1/1994 | Sugarbaker | ........ | A61B 17/3403 606/1 |
| 5,354,283 A * | 10/1994 | Bark | ...................... | A61M 25/02 128/DIG. 26 |
| 5,375,588 A * | 12/1994 | Yoon | ................... | A61B 17/3462 606/1 |
| 5,810,712 A * | 9/1998 | Dunn | ...................... | A61B 90/50 600/114 |
| 5,851,207 A * | 12/1998 | Cesarone | ........... | A61B 17/1728 606/284 |
| 6,139,550 A * | 10/2000 | Michelson | ............. | A61B 17/80 606/295 |
| 7,338,494 B2 * | 3/2008 | Ryan | ................... | A61B 17/1604 606/79 |
| 7,488,327 B2 * | 2/2009 | Rathbun | ............ | A61B 17/1728 606/96 |
| 8,066,749 B2 | 11/2011 | Winslow et al. | | |
| 8,998,988 B2 | 4/2015 | Phillips et al. | | |
| 9,198,769 B2 | 12/2015 | Perrow et al. | | |
| 9,301,785 B2 | 4/2016 | Wallenstein | | |
| 9,572,589 B2 * | 2/2017 | Knape | ....................... | A61B 17/17 |
| 10,034,771 B2 | 7/2018 | Capote et al. | | |
| 10,143,499 B2 | 12/2018 | Milz et al. | | |
| 10,159,514 B2 | 12/2018 | Perrow et al. | | |
| 10,729,556 B2 | 8/2020 | Capote et al. | | |
| 10,980,575 B2 | 4/2021 | Perrow et al. | | |
| 11,033,302 B2 | 6/2021 | Milz et al. | | |
| 2005/0015092 A1 * | 1/2005 | Rathbun | ............ | A61B 17/1757 606/96 |

(Continued)

*Primary Examiner* — David W Bates

(57) ABSTRACT

An inserter assembly for a spinal plate which includes a fastener hole for receiving a bone screw. The assembly includes an awl, and a shaft having a lumen for receiving the awl and a distal tip. A collar has a central hole for receiving the awl. A distal collar tip is adapted to be inserted into the fastener hole. An interior curved surface of the collar receives the distal tip of the shaft for polyaxial movement of the shaft relative to the collar.

12 Claims, 4 Drawing Sheets

(56) References Cited

U.S. PATENT DOCUMENTS

| | | | |
|---|---|---|---|
| 2007/0055286 A1* | 3/2007 | Ralph | A61B 17/1728 606/96 |
| 2009/0036933 A1* | 2/2009 | Dube | A61B 17/8615 606/301 |
| 2009/0326545 A1* | 12/2009 | Schaffhausen | A61B 17/8891 81/436 |
| 2019/0269418 A1* | 9/2019 | Nino | A61B 17/3403 |
| 2020/0015870 A1* | 1/2020 | Treace | A61B 17/1604 |
| 2021/0059726 A1* | 3/2021 | Artaki | A61B 17/8872 |
| 2021/0338290 A1 | 11/2021 | Milz et al. | |
| 2022/0313327 A1* | 10/2022 | Perez | A61B 17/846 |

* cited by examiner

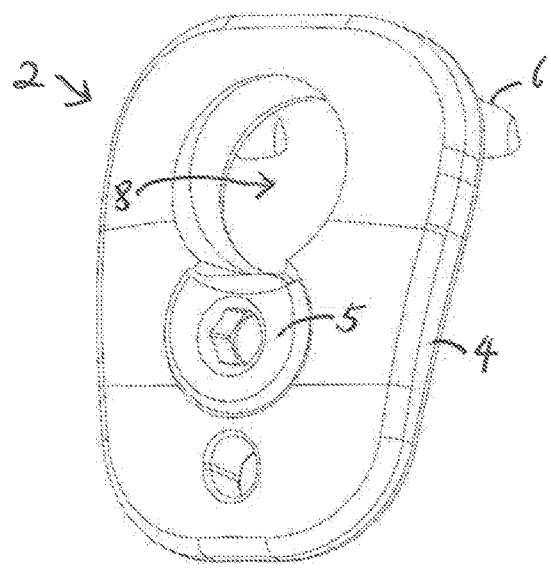
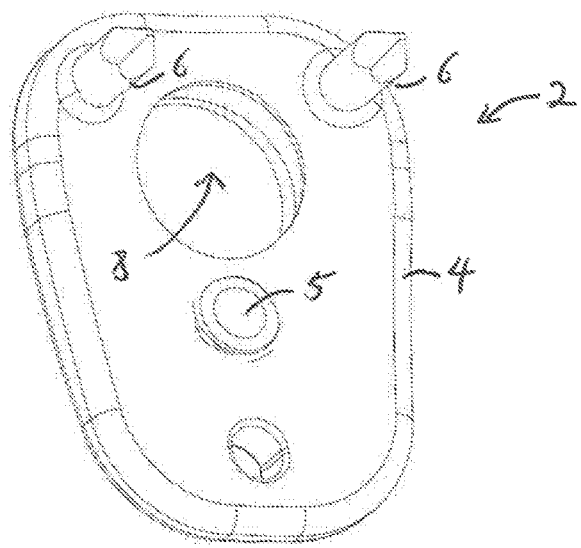
FIG. 1A    FIG. 1B
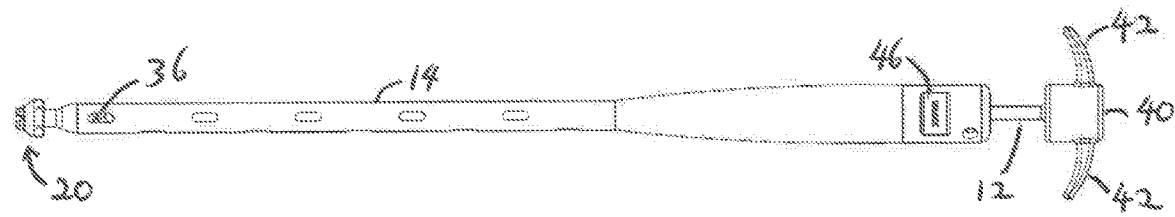
FIG. 2
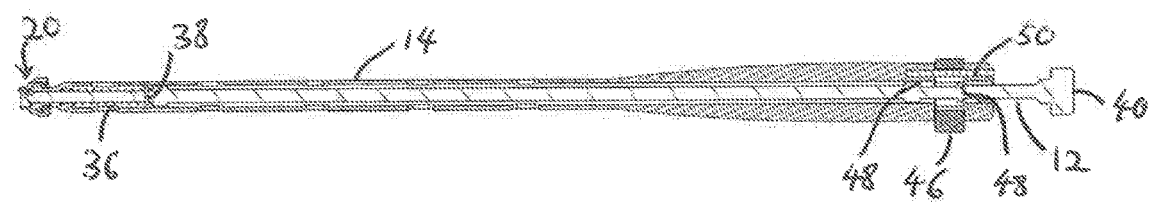
FIG. 3

PLATE INSERTER SYSTEM AND METHOD

TECHNICAL FIELD

The present invention relates to surgical instruments and, in particular, surgical devices for spinal fusion.

BACKGROUND

Bone plates are attached to outer walls of adjacent vertebral bodies of a spine. The plates such as buttress plates may be used to prevent a spinal implant such as a spacer from backing out of its position in the intervertebral space. Other plates work in conjunction with an intervertebral spacer to fuse the vertebral bodies together.

Attaching the plate involves a series of steps including use of an awl to pierce the cortical bone and then use of a drill or tap to make insertion of a bone fastener easier. In spinal surgery, surgical procedure time is an important factor due to the use of anesthesia. The design of instrumentation passed in situ are also important due to the sensitive vasculature in surrounding areas and the need for visualization by the surgeon.

Therefore, it is desirable to provide a system and method for improving the procedure time while holding the plate steady at a desirable piercing angle.

SUMMARY

An inserter assembly for a spinal plate that contains a fastener hole for receiving a bone screw. The assembly includes an awl, a shaft having a lumen for receiving the awl and a collar. A central hole of the collar receives the awl, and a distal collar tip is adapted to be inserted into the fastener hole. An interior curved surface of the collar receives the distal tip of the shaft for polyaxial movement of the shaft relative to the collar.

BRIEF DESCRIPTION OF THE DRAWINGS

FIGS. 1A and 1B are perspective top and bottom views of a buttress plate.

FIG. 2 is a side view of an inserter assembly according to one aspect of the present invention.

FIG. 3 is a cross-sectional view of the inserter assembly of FIG. 2.

DETAILED DESCRIPTION OF THE INVENTION

Figure 4:
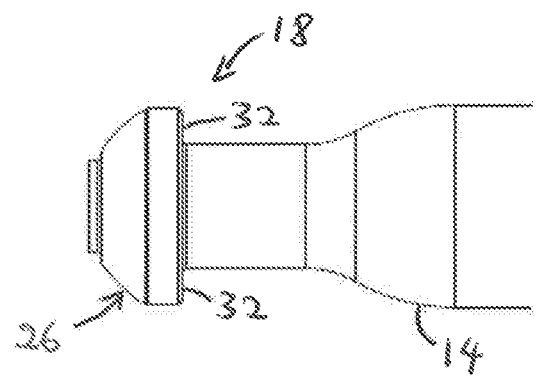
FIG. 4 is a side view of a distal tip of a shaft of the inserter assembly of FIG. 2.

The aspects of the disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the disclosure. The examples used herein are intended merely to facilitate an understanding of ways in which the disclosure may be practiced and to further enable those of skill in the art to practice the aspects of the disclosure. Accordingly, the examples and aspects herein should not be construed as limiting the scope of the disclosure, which is defined solely by the appended claims and applicable law. Moreover, it is noted that like reference numerals represent similar parts throughout the several views of the drawings.

The terms "including", "comprising" and variations thereof, as used in this disclosure, mean "including, but not limited to", unless expressly specified otherwise.

The terms "a", "an", and "the", as used in this disclosure, mean "one or more", unless expressly specified otherwise.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

A typical buttress plate 2 is shown in FIGS. 1A and 1B. The plate 2 has a body 4 having a pair of spikes 6 that are pushed through the vertebral wall, and a bone fastener hole 8 for receiving a bone screw (not shown) which is screwed through the vertebral bone. A backout lock 5 is positioned below the fastener hole 8 and can be rotated to prevent the bone screw from backing out after the bone screw has been inserted.

The buttress plate 2 is positioned against the vertebral wall with an inserter assembly 10 as shown in FIG. 2. The inserter assembly 10 includes an awl 12, a shaft 14 having a lumen 16 for receiving the awl 12 and a distal tip 18 extending distally of the shaft 14. The lumen 16 receives the awl 12 along its longitudinal axis L. The inserter assembly 10 further includes a collar 20 having a central hole 22 for receiving the awl 12 and a distal collar tip 24 adapted to be inserted into the fastener hole 8. The collar 20 has an interior curved surface 26 for receiving the distal tip 18 of the shaft 14 for polyaxial movement of the shaft 14 relative to the collar 20.

In one embodiment, the distal tip 18 of the shaft 14 has a convex surface 26 and the interior curved surface 28 of the collar 20 has a concave surface that interacts with the convex surface to provide the polyaxial movement. The convex distal tip 18 may include a spherical surface 26 and the interior concave surface 28 may include a spherical surface that interacts with the spherical surface of the distal tip 18 to provide the polyaxial movement.

Figure 5A:
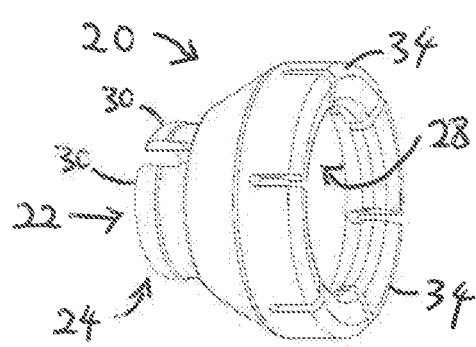
FIGS. 5A and 5B are perspective front and rear views of a collar of the inserter assembly of FIG. 2, respectively.
Figure 5B:
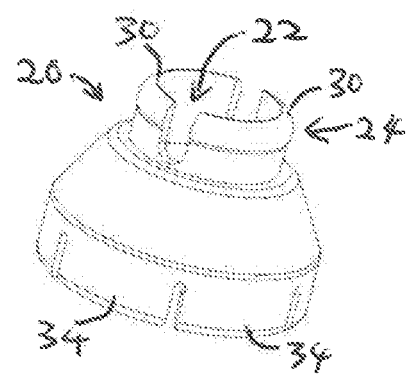

As shown in FIGS. 5A and 5B, the collar tip 24 as shown includes a plurality of circumferentially arranged tabs 30 to provide a secure fit with the fastener hole 8. The tabs 30 may be positioned to provide an interference fit with the fastener hole 8. In another embodiment, the tabs 30 are shaped to provide a resilient snap fit with the fastener hole 8. As shown, there are two tabs separated by cuts.

The tabs 30 are oversized and the cuts allow the collar 20 to spring inward and provide a solid interference fit into the fastener hole 8. The fit of the tabs 30 allows for the plate 2 to be impacted into vertebra and can distribute the load of the impaction to the face of the plate.

As shown in FIG. 4, the distal tip 18 of the shaft 14 includes a circumferentially arranged shoulder 32 and a convex surface 26 extending distally of the shoulder 32. The collar 20 may include a plurality of inwardly extending ribs 34 that retain the distal tip 18 of the shaft 14 around the shoulder 32 of the distal tip 18 of the shaft 14.

The inwardly extending ribs 34 contact the convex surface 26 and resiliently move radially outwardly as the collar 20 translates proximally and then radially inwardly over the shoulder 32 of the distal tip 18 to retain the distal tip 18 in the collar 20. As the ribs 34 move radially inwardly, they may be snap fit over the shoulder 32 to provide an auditory feedback to let the user know that the collar 20 is securely attached to the distal tip 18 of the shaft 14. As shown in FIGS. 5A and 5B, there may be six ribs 34 separated by cuts.

A spring 36 is coupled to the awl 12 with a retention pin 38 that fixes the proximal end of the spring 36 to the awl 12 to provide a spring bias in a proximal direction. A proximal portion of the awl 12 includes an impaction head 40 and a pair of wings 42 extending laterally from the impaction head. The wings 42 are used to rotate and translate the awl 12 within the shaft 14, and are especially useful when the awl 12 tip gets stuck in difficult bone.

Figure 6A:
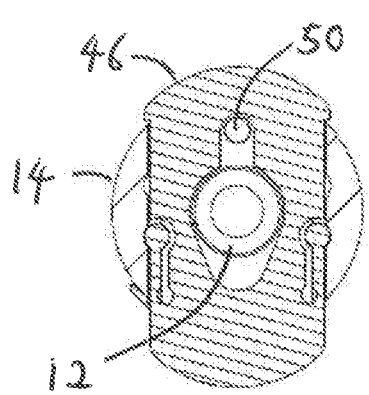
FIGS. 6A and 6B are front views respectively showing unlocked and locked positions of a lock disposed in the shaft of the inserter assembly of FIG. 2.
Figure 6B:
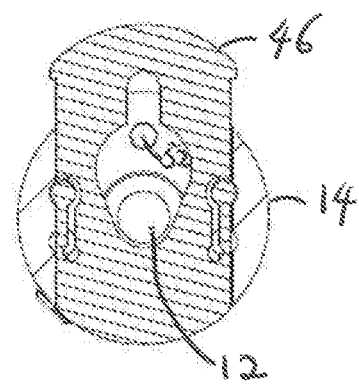

A locking mechanism 44 includes a locking button 46 and a pair of spaced locking ribs 48. The locking button 46 can be laterally slid into one of two grooved locations to either a locked or unlocked position and is slidably secured to the shaft 14 by a retention pin 50. In a locked position, the locking button 46 and the ribs 48 act together to prevent the awl 12 from translating distally past the collar 20 (see FIG. 6B). In an unlocked position, the awl 12 is able to translate past the collar 20 and into the fastener hole 8 when the impaction head is impacted.

Figure 7A:
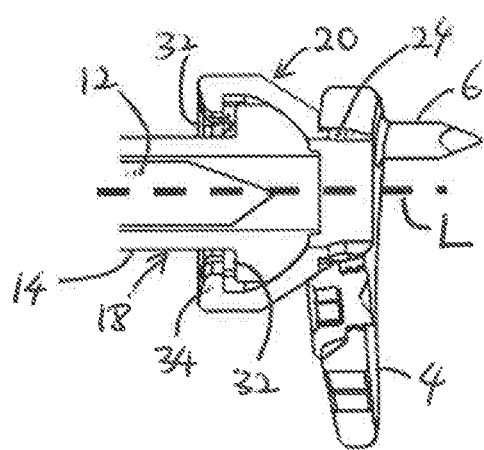
FIGS. 7A and 7B are side views of the inserter assembly attached to the plate at different angles.
Figure 7B:
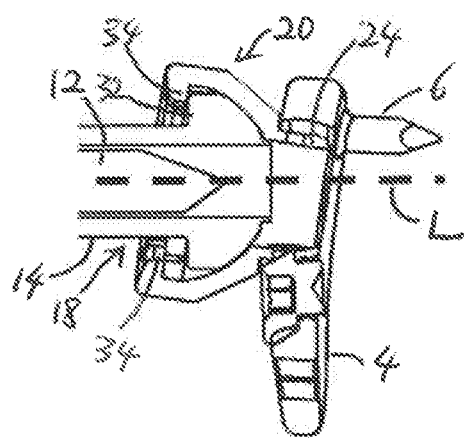
Figure 8:
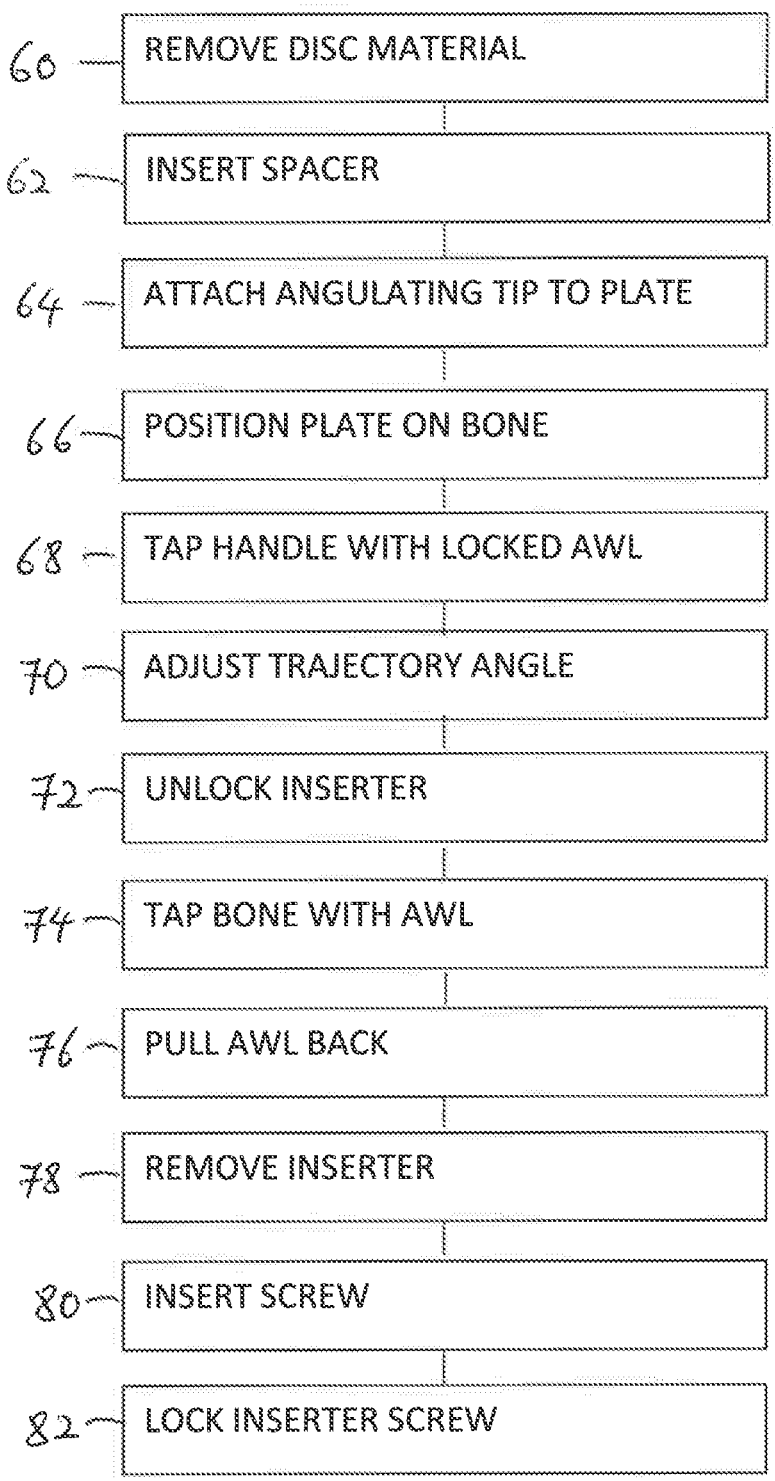
FIG. 8 is a flowchart showing a method of attaching a plate to a vertebral body according to another aspect of the present invention.

A method of attaching a bone plate 2 will now be explained with reference to FIG. 8. Prior to the procedure, the collar 20 and the awl 12 will already have been coupled to the shaft 14. In step 60, disc material is removed from an intervertebral space between two vertebral bodies to be fused, e.g., between L4 and L5 or between L5 and S1. In step 62, a spinal implant such as a spacer is inserted and positioned in the intervertebral space. In step 64, the collar 20 is attached to the bone plate 2 as shown in FIGS. 7A and 7B.

In step 66, the plate 2 with the attached inserter assembly 10 is positioned over the vertebral wall of the upper vertebral body to be fused.

In step 68, the impaction head 40 is gently tapped with the locking mechanism 44 in the locked position to push the spikes 6 of the plate 2 into the vertebral wall.

In step 70, the shaft 14 of the inserter assembly 10 is manipulated against the plate 2 to adjust the trajectory angle of the awl 12. As can be seen in FIGS. 7A and 7B, the collar 20 allows+/−8 degrees of angulation relative to the plate 2. As the shaft 14 approaches the maximum angulation, the shoulder 32 of the distal tip 18 contacts the underside of the ribs 34 in the collar 20 to prevent the shaft 14 from going past the predefined maximum angulation.

In step 72, the locking mechanism 44 is slid into the unlocked position.

In step 74, the impaction head 40 of the awl 12 is tapped to pierce the cortical bone of the upper vertebral body in order to prepare the bone screw.

In step 76, the awl 12 is pulled back to remove the awl tip from the cortical bone. This may be done by grabbing the wings 42 of the impaction head 40 with user's fingers.

In step 78, the inserter assembly 10 is then detached from the plate 2 and withdrawn as a single unit.

In step 80, a bone screw is screwed into the pierced bone.

In step 82, the backout lock 5 is rotated to lock the inserted bone screw.

As can be seen above, the advantages of the inserter assembly are many. The inserter assembly of the present invention reduces the number of procedural steps needed for plating and the number of instruments passed in situ. The inserter assembly functions as an inserter with a quick and easy spring fit into the plate's fastener hole, which ensures that the assembly does not go outside the profile of the implant and add to the exposure needed. The locking button feature provides safety so that no sharp instruments are passed in situ and the surgeon has full control on when the awl can be deployed.

It will be apparent to one skilled in the relevant arts that any of the above-described modifications may be combined. For example, a bone plate may include a sharp, peripheral ridge to enhance stability of the construct; optional spikes for further enhancing stability; and notched-head bone screws to prevent rotation of the screws inside the body. Other combinations are possible and contemplated. A bone plate or other construct or instrumentation may utilize any combination of the above-described enhancements without departing from the spirit and scope of the specification, including the attached claims.

While the disclosure has been described in terms of exemplary aspects, those skilled in the art will recognize that the disclosure can be practiced with modifications in the spirit and scope of the appended claims. These examples given above are merely illustrative and are not meant to be an exhaustive list of all possible designs, aspects, applications or modifications of the disclosure.

What is claimed is:

1. An inserter assembly for a spinal plate having a fastener hole for receiving a bone screw configured to be screwed into a vertebral bone, comprising:
   an awl comprising an impaction head and a pair of wings extending laterally from the impaction head;
   a shaft having a lumen for receiving the awl and a distal tip; and
   a collar having a central hole for receiving the awl, a distal collar tip adapted to be inserted into the fastener hole and an interior curved surface for receiving the distal tip of the shaft for polyaxial movement of the shaft relative to the collar,
   the distal tip of the shaft includes a circumferentially arranged shoulder and a convex surface extending distally of the shoulder; and
   the collar includes a plurality of inwardly extending ribs that retain the distal tip of the shaft around the shoulder of the distal tip of the shaft
   wherein the inwardly extending ribs contact the convex surface and resiliently move radially outwardly and then radially inwardly over the shoulder of the distal tip to retain the distal tip in the collar.

2. The inserter assembly of claim 1, wherein the distal tip of the shaft has a convex surface and the interior curved surface of the collar has a concave surface that interacts with the convex surface to provide the polyaxial movement.

3. The inserter assembly of claim 1, wherein the collar tip includes a plurality of circumferentially arranged tabs to provide a secure fit with the fastener hole.

4. The inserter assembly of claim 3, wherein the tabs are positioned to provide an interference fit with the fastener hole.

5. The inserter assembly of claim 1, wherein the plurality of inwardly extending ribs include only six ribs.

6. The inserter assembly of claim 1, further comprising a spring coupled to the awl to provide a spring bias in a proximal direction.

7. The inserter assembly of claim 3, wherein the plurality of circumferentially arranged tabs include only two tabs.

8. An inserter for a spinal plate having a fastener hole for receiving a bone screw configured to be screwed into a vertebral bone, comprising:
- an awl comprising an impaction head and a pair of wings extending laterally from the impaction head;
- a shaft having a lumen that receives the awl and a convex distal tip; and
- a collar having a central hole for receiving the awl, a distal collar tip adapted to be inserted into the fastener hole and an interior concave surface for receiving the convex distal tip for polyaxial movement of the shaft relative to the collar, the central hole in communication with the shaft lumen,
- the distal tip of the shaft includes a circumferentially arranged shoulder and a spherical surface extending distally of the shoulder; and
- the collar includes a plurality of inwardly extending ribs that retain the distal tip of the shaft around the shoulder of the distal tip of the shaft,
- wherein the inwardly extending ribs are configured to resiliently move radially outwardly and then radially inwardly over the shoulder of the distal tip to retain the distal tip in the collar.

9. The inserter assembly of claim 8, wherein the convex distal tip includes a spherical surface and the interior concave surface includes a spherical surface that interacts with the spherical surface of the distal tip to provide the polyaxial movement.

10. The inserter assembly of claim 8, wherein the collar tip includes a plurality of circumferentially arranged tabs to provide a secure fit with the fastener hole.

11. The inserter assembly of claim 10, wherein the tabs are positioned to provide an interference fit with the fastener hole.

12. The inserter assembly of claim 8, further comprising a spring coupled to the awl to provide a spring bias in a proximal direction.

\* \* \* \* \*